Figure 1:
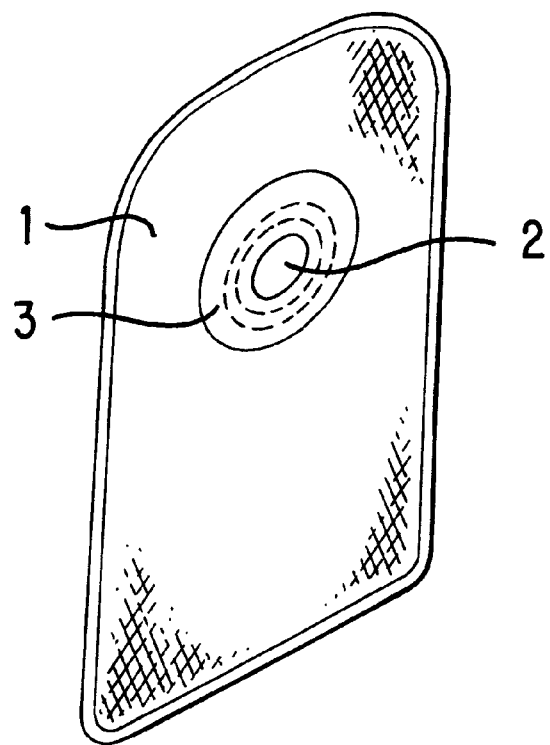

United States Patent
Quacquarella et al.

[11] Patent Number: 5,989,235
[45] Date of Patent: *Nov. 23, 1999

[54] OSTOMY BAG

[75] Inventors: Cesare Quacquarella; Livio Buongiorno, both of Milan; Vittorio Perego, Busto Arsizio, all of Italy

[73] Assignee: Cryovac, Inc., Duncan, S.C.

[*] Notice: This patent issued on a continued prosecution application filed under 37 CFR 1.53(d), and is subject to the twenty year patent term provisions of 35 U.S.C. 154(a)(2).

[21] Appl. No.: 08/903,570

[22] Filed: Jul. 31, 1997

[30] Foreign Application Priority Data

Jan. 29, 1999 [EP] European Pat. Off. ............... 96112399

[51] Int. Cl.$^6$ ....................................................... A61F 5/44
[52] U.S. Cl. ............................................. 604/332; 604/338
[58] Field of Search ....................... 604/332–345, 604/327; 427/189, 200, 206; 156/279

[56] References Cited

U.S. PATENT DOCUMENTS

| | | |
|---|---|---|
| 4,490,145 | 12/1984 | Campbell .................................. 604/333 |
| 4,816,027 | 3/1989 | Gilchrist et al. .......................... 604/339 |
| 5,316,607 | 5/1994 | Johnsen et al. ........................... 156/212 |
| 5,423,782 | 6/1995 | Wolrich ..................................... 604/339 |
| 5,545,154 | 8/1996 | Oberholtzer .............................. 604/336 |
| 5,591,144 | 1/1997 | Smith et al. ............................... 604/327 |
| 5,672,163 | 9/1997 | Ferreira et al. ........................... 604/333 |
| 5,722,965 | 3/1998 | Kuczynski ................................ 604/344 |
| 5,785,695 | 7/1998 | Sato et al. ................................. 604/339 |

*Primary Examiner*—John G. Weiss
*Assistant Examiner*—Dennis Ruhl
*Attorney, Agent, or Firm*—Elda DeCarli; Thomas C. Lagaly

[57] ABSTRACT

The invention provides a drainage bag (colostomy, ileostomy or urostomy bag) comprising a bag of thermoplastic material having means to define an opening for receiving waste material from a stoma and means to secure the bag in place with the opening connected to the stoma, characterized in that at least the surface of the bag in contact with the skin of the wearer is flocked. Also described is an ostomy appliance comprising a re-usable outer bag and a disposable inner bag, means for securing the two bags together and to the stoma, means for inserting and removing the inner bag from the outer one, and means for closing, the outer bag once the inner one is in place, characterized in that at least the surface of the outer bag in contact with the skin of the wearer is flocked.

11 Claims, 2 Drawing Sheets

OSTOMY BAG

The present invention relates to ostomy bags that can be confortably worn by the patients.

An ostomy bag is a pouch that is employed to collect waste material that exits a person's body through a stoma, i.e. through an artificial, permanent, opening, surgically created in the ostomate's skin and connected to the intestine or to the bladder.

Colostomy, ileostomy, and urostomy bags, herein collectively referred to as ostomy bags, typically comprise a pouch of plastic, moisture-impermeable and odor-barrier, material; an opening in said bag to allow waste material to enter into the plastic envelope; and means to secure the bag in place with the opening connected to the stoma. This can be obtained by means of a tape that is heat bonded to the ostomy bag around the opening; said tape has an opening which is positioned in-line with the opening of the bag and the side of said tape which is adjacent to the ostomate's body is coated with an adhesive which allows adhesion of the ostomy appliance to the "peristomal area", i.e., the skin area surrounding the stoma.

Preferably the means to secure the ostomy bag to the stoma and the ostomy bag itself, are constructed as two separable parts which are connected and disconnected by the user as desired. This is achieved for instance by applying to the ostomate's skin by means of a suitable adhesive a tape that bears on its outer surface a semi-rigid plastic snap ring, bonded by conventional means to the tape, that surrounds the opening. The ostomy bags then bear a second complementary snap ring mating with the tape one; said complementary snap ring is bonded to the ostomy bag and surrounds the opening therein. The user can therefore apply and remove the ostomy bag from the stoma without peeling off from the skin the means for securing the bag to the stoma. When assembled the snap ring provides a tight leak-free seal.

Figure 2:
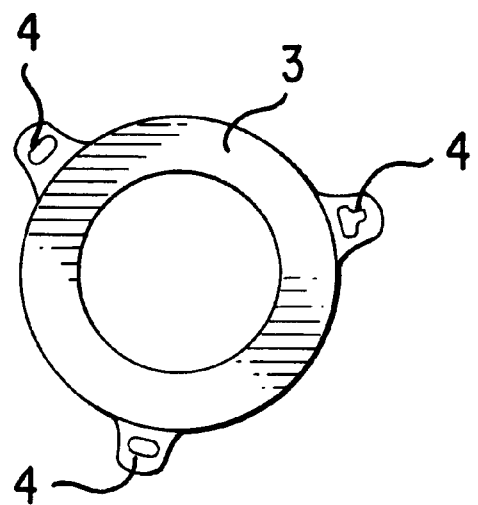

For the sake of clarity, FIGS. 1 and 2 in the attached drawings illustrate a conventional design for ostomy bags.

In FIG. 1, (1) represents the odor-barrier thermoplastic pouch, (2) is the opening in the pouch that needs to be in-line with the stoma in order to receive the body's waste material, and (3) is the tape that is welded to the pouch and is used to secure the pouch in place by adhering to the ostomate's peristomal skin. In a preferred aspect, as indicated above, the ostomy bag and the means to secure it to the patient's skin are constructed as two separate parts. In such a case, in FIG. 1, (3) represents a ring-shaped flange of semi-rigid plastic as better described in FIG. 2. This pouch strap ring, that preferably has clip retainers (4) spaced thereon, is used to secure the pouch to a tape, applied to the ostomate's skin through its adhesive surface, said last tape bearing a mating ring on its outer surface (not shown in the drawings).

In all events the ostomy bag, which has a surface larger than that of the tape for attachment, lies on the ostomate's skin, conforming the abdominal contours and moving with the skin as the skin moves.

The most common plastic films that are ordinarily employed in the manufacture of ostomy bags, being essentially impermeable to moisture vapor, do not allow the skin to breathe and frequently give rise to irritation of the user's skin, particularly in case of a consistent and prolonged contact therewith.

Different solutions have been proposed to solve this problem, such as the use of a fabric material as the skin contact layer (as in CA-A-1,060,749) or the use of a composite thermoplastic with a skin contact layer of a thermoplastic non-woven material (as in EP-A-433,060).

A great challenge still exists however to further improve the ostomates' comfort providing ostomy bags that not only meet functional requirements such as good mechanical resistance, easy sealability, and adequate odor barrier properties, but also are as much comfortable for the patient to wear as possible.

It has now been found that by using in the manufacture of an ostomy bag, at least for the surface thereof which is in contact with the patient's skin, a thermoplastic material which has been flocked, the discomfort which is associated with prolonged contact of moisture impermeable material with the patient's skin is remarkably alleviated.

Flocking (flock coating or flock lining) is a technique that allows the coating of a substrate with a high number of short fibers to give to the finished article a suede- or velvet-like appearance and touch.

In said process, the substrate to flocked is first coated with a suitable glue or adhesive; then, in an electrostatic field, a great number of individual fibers (flock) are shot vertically into the thick adhesive coating; the flocked surface is then dried and cooled; and the excess flock is sifted out. Electrostatic flocking is based on the law of physics. The rod-shaped flocks take over the charge at one pole (due to either ionization or electrostatic induction) and then travel to the counterpole (the substrate coated with the adhesive) aligning themselves along the lines of force that always enter the substrate vertically.

Flocking machines and production lines for flocking that can be used in the manufacture of the flocked material for the ostomy bag of the present invention are commercially available. An example of a suitable flocking machine is Flocking machine GFS manufactured by Maag Flockmaschinen GmbH.

For the use according to the present invention the substrate or base to be flocked is a thermoplastic mono- or multi-layer film.

Widely differing kinds of fibers can be employed, such as polyamides, polyesters, acrylic polymers, and natural fibers, e.g. cotton and viscose. In a preferred embodiment of the present invention a natural fiber is employed, and even more preferably cotton fibers are used. The length of these fibers is typically less than 5 mm and generally of from about 0.1 to about 3.0 mm. Fibers of from about 0.3 to about 1.5 mm are preferred. The amount of flock fibers distributed per $m^2$ of substrate may vary depending on the type of fibers employed, on the line speed and on the more-or-less heavy loading of the substrate which is desired. For the purposes of the present invention, optimum results are obtained with from about 10 to about 100 $g/m^2$ and particularly with from about 30 to about 70 $g/m^2$ of flock fibers, because a remarkable improvement in hand-feel and appearance is obtained with little increase in weight or stiffness. Fibers of different thickness can also be employed in the manufacture of the ostomy bag according to the present invention. The difference in thickness of the fibers is indicated as the titer which is measured in dtex or grams per 10,000 m length of the individual fiber. For the purpose of the present invention fibers with a titer of from about 2 to about 20 can suitably be employed.

Suitable adhesives will be selected depending on the type of substrate and flock fibers employed. In general said adhesive must be electrically conductive and must remain adhesive on the substrate surface for a time sufficient to allow the vertical fibers to penetrate. It is typically applied to the substrate with a sprayer or by brush, roller, pad or squeegee. Acrylic adhesives, such as polyacrylates or polyacrylates modified with epoxy resins, and urethane adhesives are non limitative examples of suitable adhesives. Alternative adhesives that may suitably be employed include e.g. PVC plastisol adhesives and chlorinated modified polyolefin adhesives.

While the use of a wholly flocked surface in contact with the ostomate's skin provides for optimum comfort of the wearer, it might nevertheless be useful to leave parts of the surface unflocked. As an example leaving small areas of the surface unflocked will allow visual monitoring of the bag contents. Partial flocking can easily be achieved by distributing the adhesive only in the areas to be flocked.

As indicated above, the substrate which is flocked is a mono- or multi-layer thermoplastic film.

In one embodiment of the present invention the substrate is an odor-barrier thermoplastic material, comprising at least one layer of an odor-barrier material, such as PVdC (a copolymer of vinylidene chloride with at least one comonomer copolymerisable therewith), EVOH (ethylene-vinyl alcohol copolymer), PVOH (polyvinyl alcohol), and polyamides or polyamide co- or ter-polymers.

Generally these odor-barrier films comprise, besides the odor-barrier layer, at least one additional outer sealing layer. Generally polyethylenes, linear polyethylenes, ethylene-vinyl acetate copolymers, ethylene-alkyl acrylate copolymers, ethylene-alkyl methacrylate copolymers, polyurethanes or blends thereof are employed for the sealing layer. The polar copolymers and particularly ethylene-vinyl acetate copolymers and polyurethanes, are normally preferred because they are sealable also by Radio Frequency which is a sealing method widely used in this area.

A preferred odor-barrier thermoplastic film that can be flocked and used in the manufacture of ostomy bags according to the present invention comprises three layers, the outer layers comprising an ethylene-vinyl acetate copolymer, preferably with a high content of vinyl acetate units (e.g. 18 or more w. % of VA units), and the core layer being of PVdC. Tie layers may as well be included in this structure, interposed between the core odor-barrier layer and the outer EVA skin layers.

An alternative odor-barrier structure that can suitably be flocked and employed in the manufacture of ostomy bags according to the present invention is a 5-layer structure with a PVdC core layer, polyethylene skin layers and intermediate tie layers.

EVOH, PVOH, and polyamide homo-, co-, or ter-polymer odorbarrier layers may suitably be employed when a chlorine-free structure is desired. Examples of suitable chlorine-free odor-barrier substrates are described for instance in the following patents or patent applications: DE-A-4,100,350, WO-A-93/11938, DD-B-274,386, DD-B-274,387, and EP-A-700,777.

The thickness of the barrier layer as well as that of the other layers in the multi-layer odor-barrier structures to be flocked will be suitably selected, as known in the field, depending on the desired mechanical and odor-barrier properties. In general the thickness of the barrier layer may range from about 4 to about 10 microns, depending on the type of material used to impart odor-barrier properties to the structure. The overall thickness of the substrate will generally range from about 40 to about 200 microns, typically from about 50 to about 130 microns, and preferably from about 60 to about 100 microns.

The flocked odor-barrier substrate can be employed in the manufacture of ostomy bags by methods well known in the art.

In particular, both the skin contact surface and the opposite outer surface of the ostomy bag can be of flocked material. Alternatively the flocked material can be employed for the skin contact surface only, while the outer surface can be made by the same, unflocked, thermoplastic film or by another odor-barrier film, provided the inner surfaces of the two films can be welded together.

The obtained ostomy bag can be provided at the bottom with a drain fitting, such as an integral cap which is opened to drain the bag, when a washable, re-usable, bag is desired.

It is also possible to use the flocked odor-barrier substrate for the manufacture of an outer bag that is used as a cover and holder of an inner, disposable, ostomy pouch.

In such a case the outer flocked bag will provide for the patient's comfort and for at least part of the odor-barrier properties of the overall ostomy appliance.

Said outer bag will be provided with a reclosable cut-out, either horizontally or vertically, generally a slit along one of the bag edges, to allow access of the inner ostomy pouch. The hole of both the outer and the inner bags will be in-line with the stoma, and the outer and inner pouches will be detachably secured one to the other and to the stoma. To take advantage of the odor-barrier properties of the outer flocked bag, the means for closing the outer bag once the inner one is in place as well as the means for securing the two bags together and to the stoma should be designed not to allow passage of air in-between.

As for the reclosable slit, air-tightness can be achieved e.g. by a couple of mating closure strips, positioned on the inner, facing, surfaces of the slitted edges. One strip comprises the male or rib portion which interlocks into the female or grooved portion of the other strip. The ribs and groove portions of the closure strips are easily separable by the fingers of the patient when the filled inner pouch needs to be removed and discarded and can be easily interlocked by snap fitting the male ribs into the corresponding female portion once a new empty inner pouch has been put in place. Alternatively the desired tightness can be provided by an adhesive odor-barrier patch that is used to entirely cover the slit.

Figure 4:
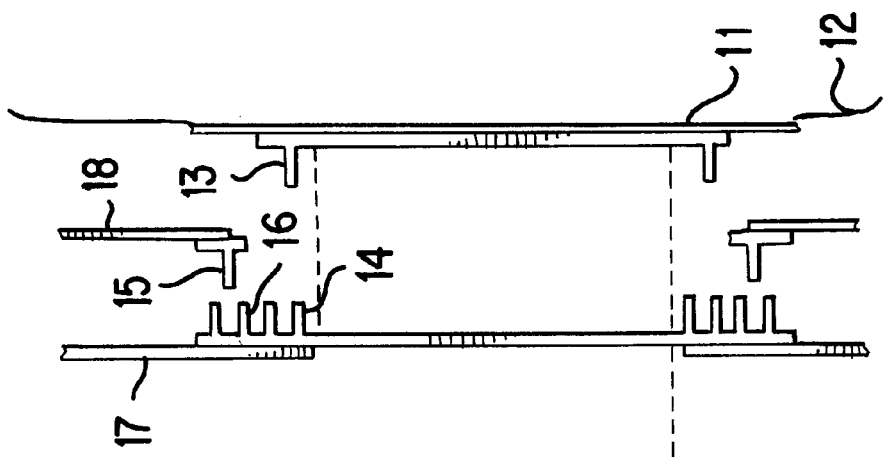
Figure 3:
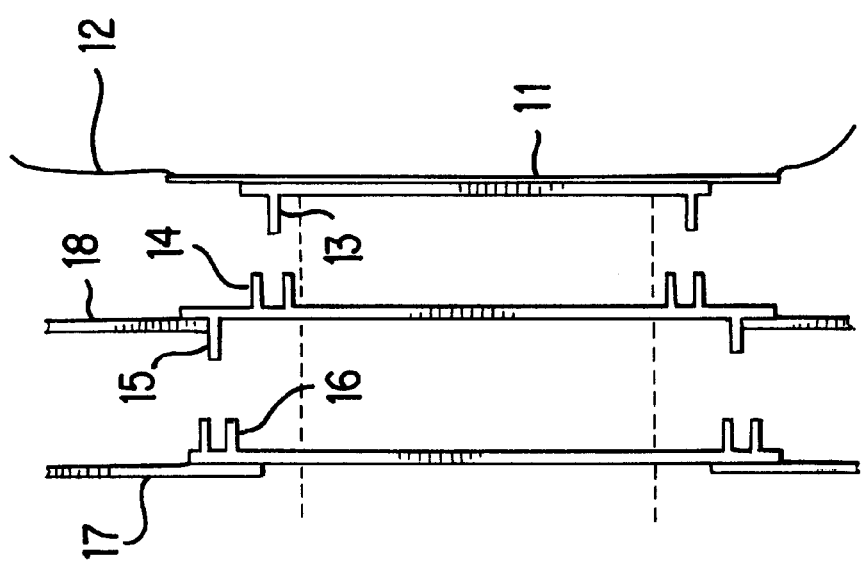

As for the connection of the inner and outer bags to the stoma, FIGS. 3 and 4 represent a side view of two different ways of achieving an air-tight, leak-free, connection.

In both cases the overall ostomy appliance is releasably secured to the peristomal area by means of an adhesive tape (11) applied to the patient's body (12), said tape being equipped with a plastic ring (13) that snap fits into a corresponding mating ring (14) positioned on the outer bag in the embodiment of FIG. 3 and on the inner bag in the embodiment of FIG. 4. The system of plastic rings that interlock to tightly secure the inner disposable bag to the outer re-usable one is indicated as (15) and (16). The thermoplastic film of the inner bag is indicated as (17) while (18) is the flocked skin contact surface of the outer bag.

If desired, the ostomy appliance according to the above preferred embodiment of the invention can be more securely attached to the stoma by fastening it to a waist encircling belt, e.g. by means of Velcro patches.

The use of an outer odor-barrier bag allows to decrease the thickness of the odor-barrier layer in the inner, disposable, ostomy pouch. In terms of odor-barrier properties, the results obtained with an ostomy appliance as in said preferred embodiment of the present invention are better than those obtained with a conventional ostomy pouch having an odor-barrier layer thick as the sum of the barrier layers in the separate outer and inner bags.

It would also be possible to use inner chlorine-free ostomy pouches coupled to an outer re-usable PVdC-containing bag. The inner pouches could more safely be disposed of, owing to the absence of a chlorine-containing layer, while the problem of the limited odor-barrier properties of EVOH, PVOH or polyamides would be overcome by the use of an outer bag with better odor-barrier properties. As an example it could be possible to use a toilet flushable PVOH-based inner ostomy pouch, with an outer re-usable bag with a PVdC barrier layer.

Furthermore, since the use of a flocked outer bag, besides increasing the comfort of the wearer, also provides for a sort of protection of the inner bag, the mechanical properties of the inner bag need not be as high as in a conventional ostomy bag and it is therefore possible to decrease the thickness of the film layers in the inner bag. It is thus possible to reduce the amount of plastic waste that needs to be disposed of.

In the ostomy appliance according to the above preferred embodiment, the inner bag might be devoid of an odor-barrier layer. It is however preferred to use an inner bag with an odor-barrier layer at least about 2 micron thick. More preferably, the thickness of said barrier layer in the inner bag would be at least about 3 microns, and typically it is of from about 3 microns to about 5 microns when PVdC is used as the barrier material and from about 3 to about 10 microns when other odor-barrier materials are employed. Depending on the thickness of the odor-barrier layer (if any) in the inner bag, the thickness of the barrier layer in the outer bag may be as low as 2 microns, preferably at least 2.5 microns, typically from about 3 to about 8 microns.

The overall thickness of the inner bag may be reduced down to 35 microns, even if preferably the overall thickness of the inner pouch will be at least 40 microns and typically will be comprised between about 45 and about 75 microns. The overall thickness of the substrate of the outer bag can be as low as 25 microns, but preferably it is comprised between about 35 and about 100 microns.

In another embodiment of the present invention, the substrate to be flocked is not odor-barrier and the obtained material is employed as the outer bag in an ostomy appliance coupled with an inner odor-barrier disposable pouch. In this case, as the outer bag has no odor-barrier properties it is necessary to use an inner ostomy pouch with the desired barrier properties. There would be therefore no purpose and no need to provide in the outer bag for a reclosable slit to insert the inner pouch or for an air-tight connection between the two bags. In this case, as the aim of the outer ostomy bag is only to improve patient's comfort, the outer bag can simply be secured to the inner one by inserting the plastic ring of the inner bag through a hole of suitable size in the outer bag before snap fitting it to the plastic ring of the adhesive tape positioned around the stoma. Furthermore the inner bag can be inserted into the outer one through a slit cut-out, horizontally or vertically, preferably in the surface of the outer bag opposite to the skin contact one. There is no need in such a case to provide for a tight closure of this slit.

In this case the substrate can be any thermoplastic film, either mono- or multi-layer. The thermoplastic material used as the substrate to be flocked is not critical and reasonably cheap resins such as ethylene-vinyl acetate copolymer, polyethylene, linear polyethylene and the like resins can suitably be employed. The thickness of the substrate will generally be comprised between about 20 and about 100 microns.

Also in this case however the thickness of the layers different from the barrier one in the inner ostomy pouch can be reduced due to the lowered demand for mechanical properties. As a consequence thereof also the amount of plastic material that needs to be disposed, will be reduced.

If desired, the outer bag may be fastened to a waist encircling belt as indicated before. Alternatively, in this embodiment of a non-barrier outer bag, said bag may be shaped as a back panel, integral with the belt, with a hole to provide access of the inner pouch hole to the stoma, and a front panel with releasable fastening means for attaching the front panel to the belt, said back and front panels defining a pocket at their lower ends for supporting the inner odor-barrier ostomy pouch, wherein at least the surface of the back panel adjacent to the ostomate's skin is flocked.

We claim:

1. An ostomy bag comprising:

a bag of thermoplastic material having an outer surface;

means to define an opening for receiving waste material from a stoma;

means to secure the bag in place with the opening connected to the stoma; and a flock coating on at least a portion of the outer surface of said bag of thermoplastic material, said flock coating comprising an adhesive coating adhered directly to said outer surface of said bag and a plurality of individual fibers adhered to said adhesive coating.

2. The ostomy bag of claim 1 wherein the fibers used for flocking are selected from polyamide fibers, polyester fibers, fibers of acrylic polymers and natural fibers.

3. The ostomy bag of claim 2 wherein the fibers used for flocking are cotton or viscose fibers.

4. The ostomy bag of claim 1 wherein the length of the fibers used for flocking is comprised between about 0.1 and about 3.0 mm.

5. The ostomy bag of claim 4 wherein the length of the fibers is of from about 0.3 to about 1.5 mm.

6. The ostomy bag of claim 1 wherein the amount of flock fibers is from about 10 to about 100 $g/m^2$.

7. The ostomy bag of claim 6 wherein the amount of flock fibers is from about 30 to about 70 $g/m^2$.

8. The ostomy bag of claim 1 wherein said thermoplastic material is an odor-barrier thermoplastic material.

9. The ostomy bag of claim 8 wherein the odor-barrier thermoplastic material is a multi-layer material comprising at least one layer of an odor-barrier polymer selected from the group consisting of PVDC, EVOH, PVOH, and polyamide homo-, Co-, or ter-polymers.

10. The ostomy bag of claim 9 wherein the odor-barrier thermoplastic material comprises two outer layers comprising an ethylene-vinyl acetate copolymer and a core odor-barrier layer of PVdC.

11. The ostomy bag of claim 10 wherein said fibers are selected from the group consisting of cotton or viscose fibers and said adhesive coating comprises a polyacrylate adhesive.

* * * * *